(12) United States Patent
Agarwal et al.

(10) Patent No.: US 7,399,760 B2
(45) Date of Patent: Jul. 15, 2008

(54) PYRIMIDINEDIONE DERIVATIVES

(75) Inventors: Shiv Kumar Agarwal, Chennai (IN); Ravikumar Tadiparthi, Chennai (IN); Pawan Aggarwal, Chennai (IN); Savithiri Shivakumar, Chennai (IN)

(73) Assignee: Bexel Pharmaceuticals Inc., Union City, CA (US)

( * ) Notice: Subject to any disclaimer, the term of this patent is extended or adjusted under 35 U.S.C. 154(b) by 2 days.

(21) Appl. No.: 11/414,229

(22) Filed: May 1, 2006

(65) Prior Publication Data

US 2006/0194799 A1    Aug. 31, 2006

Related U.S. Application Data

(62) Division of application No. 10/409,153, filed on Apr. 9, 2003, now Pat. No. 7,101,873.

(30) Foreign Application Priority Data

Apr. 10, 2002    (IN)    .................... 266/2002

(51) Int. Cl.
    *A61K 31/54*    (2006.01)
(52) U.S. Cl. ................ 514/228.2; 514/151; 544/97
(58) Field of Classification Search .............. 514/228.2, 514/151; 544/97
    See application file for complete search history.

(56) References Cited

U.S. PATENT DOCUMENTS

| 4,171,429 | A |   | 10/1979 | Watanabe et al. |
| 4,495,349 | A | * | 1/1985 | Skulnick et al. ............. 544/97 |
| 4,507,302 | A |   | 3/1985 | Fast et al. |
| 4,593,030 | A | * | 6/1986 | Skulnick et al. ............ 514/269 |
| 4,625,028 | A | * | 11/1986 | Smith ........................ 544/309 |
| 5,461,060 | A |   | 10/1995 | Miyasaka et al. |
| 7,101,873 | B2 | * | 9/2006 | Agarwal et al. .......... 514/227.8 |
| 2003/0225075 | A1 |   | 12/2003 | Agarwal et al. |

FOREIGN PATENT DOCUMENTS

DE    2142317    3/1973

OTHER PUBLICATIONS

Andreichikov et al., Chemistry of oxalyl derivatives of methyl ketones. 40. Reaction of 5-aryl-2,3-dihydro-2,3-furandiones with aryl- and aroylcyanamides, Khimiya Geterotsiklicheskikh Soedinenii (1985), (2), 166-169, See Abstract.*

Andreichikov et al. (2), Synthesis and antiinflammatory activity of 5-phenacylidene-2-imino-4-oxazolidones, Khimiko-Farmatsevticheskii Zhurnal (1989), 23(2), 157-160, See Abstract.*

Skulnick et al., "Regiospecific Synthesis of N-1 and N-2 Substituted Pyrimidinones Employing a Novel 1,3-Oxazine Prepraration", Heterocycles, vol. 23, No. 7, pp. 1685-1689 (1985).

Kamela, Journal f. Prakt. Chemie Band 324, Heft 1, 1982, S. 172-176.

Pelletier, et al., "Cytokines and Their Role in the Pathophysiology of Osteoarthritis," *Frontiers in Bioscience*, 1999, 4, 694-703.

Rabinowitz, et al., "Design of Selective and Soluble Inhibitors of Tumor Necrosis Factor-α Converting Enzyme (TACE)," *J. Med. Chem.*, 2001, 44, 4252-4267.

Russo, et al., "TNF-α as a Promising Therapeutic Target in Chronic Asthma: a Lesson From Rheumatoid Arthritis," *Clinical Science*, 2005, 109, 135-142.

Sakai, et al., "TNF-α Augments the Expression of RhoA in the Rat Bronchus," *J. Smooth Muscle Res.*, 2004, 40(1), 25-34.

Rana, et al., "Chronic Obstructive Pulmonary Disease, Asthma, and Risk of Type 2 Diabetes in Women," *Diabetes Care*, 2004, 27(10), 2478.

* cited by examiner

*Primary Examiner*—Yvonne Eyler
*Assistant Examiner*—Chukwuma O Nwaonicha
(74) *Attorney, Agent, or Firm*—Oliff & Berridge, PLC

(57) ABSTRACT

Pyrimidinedione derivatives of the general formula (I), their derivatives, analogs, tautomeric forms, stereoisomers, polymorphs, hydrates, solvates, pharmaceutically acceptable salts and pharmaceutically acceptable compositions containing them are useful for the treatment of inflammation and immunological diseases.

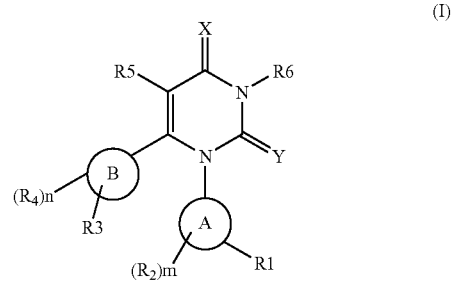

(I)

10 Claims, No Drawings

PYRIMIDINEDIONE DERIVATIVES

This is a divisional application of U.S. patent application Ser. No. 10/409,153, filed on Apr. 9, 2003, now U.S. Pat. No. 7,101,873, which is incorporated herein in its entirety by reference.

FIELD OF THE INVENTION

The present invention relates to novel pyrimidinedione derivatives of the general formula (I), their derivatives, their analogs, their tautomeric forms, their stereoisomers, their polymorphs, their hydrates, their solvates, their pharmaceutically acceptable salts and pharmaceutically acceptable compositions containing them. The present invention more particularly provides novel pyrimidinedione derivatives of the general formula (I).

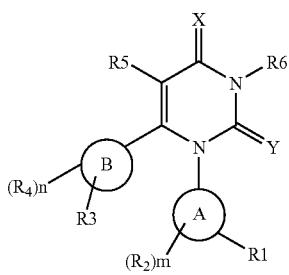

The present invention also provides a process for the preparation of the above said novel pyrimidinedione derivatives of the formula (I) pharmaceutically acceptable salts, their derivatives, their analogs, their tautomeric forms, their stereoisomers, their polymorphs, their hydrates, their solvates, their pharmaceutically acceptable salts, and pharmaceutical compositions containing them.

The novel pyrimidinedione derivatives of the present invention are useful for the treatment of inflammation and immunological diseases. Particularly the compounds of the present invention are useful for the treatment of inflammation and immunological diseases those mediated by cytokines such as TNF-α, IL-1, IL-6, IL-1β, IL-8 and cyclooxygenase such as COX-2 and COX-3. The compounds of the present invention are also useful for the treatment of rheumatoid arthritis; osteoporosis; multiple myeloma; uveititis; acute and chronic myelogenous leukemia; ischemic heart disease, atherosclerosis, cancer, ischemic-induced cell damage, pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; type I and type II diabetes; bone resorption diseases; ischemia reperfusion injury; atherosclerosis; brain trauma; multiple sclerosis; cerebral malaria; sepsis; septic shock; toxic shock syndrome; fever and myalgias due to infection; and diseases mediated by HIV-1; HIV-2; HIV-3; cytomegalovirus (CMV); influenza; adenovirus; the herpes viruses (including HSV-1, HSV-2) and herpes zoster viruses.

BACKGROUND OF THE INVENTION

It has been reported that Cyclooxygenase enzyme exists in three isoforms, namely, COX-1, COX-2 and COX-3. COX-1 enzyme is essential and primarily responsible for the regulation of gastric fluids whereas COX-2 enzyme is present at the basal levels and is reported to have a major role in the prostaglandin synthesis for inflammatory response. These prostaglandins are known to cause inflammation in the body. Hence, if the synthesis of these prostaglandins is stopped by way of inhibiting COX-2 enzyme, inflammation and its related disorders can be treated. COX-3 possesses glycosylation-dependent cyclooxygenase activity. Comparison of canine COX-3 activity with murine COX-1 and COX-2 demonstrated that this enzyme is selectively inhibited by analgesic/antipyretic drugs such as acetaminophen, phenacetin, antipyrine, and dipyrone, and is potently inhibited by some nonsteroidal antiinflammatory drugs. Thus, inhibition of COX-3 could represent a primary central mechanism by which these drugs decrease pain and possibly fever. Recent reports show that inhibitors of COX-1 enzyme causes gastric ulcers, where as selective COX-2 and COX-3 enzyme inhibitors are devoid of this function and hence are found to be safe.

The present invention is concerned with treatment of immunological diseases or inflammation, notably such diseases are mediated by cytokines or cyclooxygenase. The principal elements of the immune system are macrophages or antigen-presenting cells, T cells and B cells. The role of other immune cells such as NK cells, basophils, mast cells and dendritic cells are known, but their role in primary immunologic disorders is uncertain. Macrophages are important mediators of both inflammation and providing the necessary "help" for T cell stimulation and proliferation. Most importantly macrophages make IL-1, IL-12 and TNF-α all of which are potent pro-inflammatory molecules and also provide help for T cells. In addition, activation of macrophages results in the induction of enzymes, such as cyclooxygenase-2 (COX-2) and cyclooxygenase-3 (COX-3), inducible nitric oxide synthase (iNOS) and production of free radicals capable of damaging normal cells. Many factors activate macrophages, including bacterial products, superantigens and interferon gamma (IFN γ). It is believed that phosphotyrosine kinases (PTKs) and other undefined cellular kinases are involved in the activation process.

Cytokines are molecules secreted by immune cells that are important in mediating immune responses. Cytokine production may lead to the secretion of other cytokines, altered cellular function, cell division or differentiation. Inflammation is the body's normal response to injury or infection. However, in inflammatory diseases such as rheumatoid arthritis, pathologic inflammatory processes can lead to morbidity and mortality. The cytokine tumor necrosis factor-alpha (TNF-α) plays a central role in the inflammatory response and has been targeted as a point of intervention in inflammatory disease. TNF-α is a polypeptide hormone released by activated macrophages and other cells. At low concentrations, TNF-α participates in the protective inflammatory response by activating leukocytes and promoting their migration to extravascular sites of inflammation (Moser et al., J Clin Invest, 83, 444-55, 1989). At higher concentrations, TNF-α can act as a potent pyrogen and induce the production of other pro-inflammatory cytokines (Haworth et al., Eur J Immunol, 21, 2575-79, 1991; Brennan et al., Lancet, 2, 244-7, 1989). TNF-α also stimulates the synthesis of acute-phase proteins. In rheumatoid arthritis, a chronic and progressive inflammatory disease affecting about 1% of the adult U.S. population, TNF-α mediates the cytokine cascade that leads to joint damage and destruction (Arend et al., Arthritis Rheum, 38, 151-60,1995). Inhibitors of TNF-α, including soluble TNF receptors (etanercept) (Goldenberg, Clin Ther, 21, 75-87, 1999) and anti-TNF-α antibody (infliximab) (Luong et al., Ann Pharmacother, 34, 743-60, 2000), have recently been approved by the U.S. Food and Drug Administration (FDA) as agents for the treatment of rheumatoid arthritis.

Elevated levels of TNF-α have also been implicated in many other disorders and disease conditions, including cachexia, septic shock syndrome, osteoarthritis, inflammatory bowel disease such as Crohn's disease and ulcerative colitis etc.

Elevated levels of TNF-α and/or IL-1 over basal levels have been implicated in mediating or exacerbating a number of disease states including rheumatoid arthritis; osteoporosis; multiple myeloma; uveititis; acute and chronic myelogenous leukemia; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; type I and type II diabetes; bone resorption diseases; ischemia reperfusion injury; atherosclerosis; brain trauma; multiple sclerosis; cerebral malaria; sepsis; septic shock; toxic shock syndrome; fever, and myalgias due to infection. HIV-1, HIV-2, HIV-3, cytomegalovirus (CMV), influenza, adenovirus, the herpes viruses (including HSV-1, HSV-2), and herpes zoster are also exacerbated by TNF-α.

It can be seen that inhibitors of TNF-α are potentially useful in the treatment of a wide variety of diseases. Compounds that inhibit TNF-α have been described in several patents.

Excessive production of IL-6 is implicated in several disease states, it is highly desirable to develop compounds that inhibit IL-6 secretion. Compounds that inhibit IL-6 have been described in U.S. Pat. Nos. 6,004,813; 5,527,546 and 5,166,137.

The cytokine IL-1β also participates in the inflammatory response. It stimulates thymocyte proliferation, fibroblast growth factor activity, and the release of prostaglandin from synovial cells. Elevated or unregulated levels of the cytokine IL-1β have been associated with a number of inflammatory diseases and other disease states, including but not limited to adult respiratory distress syndrome, allergy, Alzheimer's disease etc. Since overproduction of IL-1β is associated with numerous disease conditions, it is desirable to develop compounds that inhibit the production or activity of IL-1β.

In rheumatoid arthritis models in animals, multiple intra-articular injections of IL-1 have led to an acute and destructive form of arthritis (Chandrasekhar et al., Clinical Immunol Immunopathol. 55, 382, 1990). In studies using cultured rheumatoid synovial cells, IL-1 is a more potent inducer of stromelysin than TNF-α. (Firestein, Am. J. Pathol. 140, 1309, 1992). At sites of local injection, neutrophil, lymphocyte, and monocyte emigration has been observed. The emigration is attributed to the induction of chemokines (e.g., IL-8), and the up-regulation of adhesion molecules (Dinarello, Eur. Cytokine Netw. 5, 517-531, 1994).

In rheumatoid arthritis, both IL-1 and TNF-α induce synoviocytes and chondrocytes to produce collagenase and neutral proteases, which leads to tissue destruction within the arthritic joints. In a model of arthritis (collagen-induced arthritis (CIA) in rats and mice) intra-articular administration of TNF-α either prior to or after the induction of CIA led to an accelerated onset of arthritis and a more severe course of the disease (Brahn et al., Lymphokine Cytokine Res. 11, 253, 1992; and Cooper, Clin. Exp. Immunol. 898, 244, 1992).

IL-8 has been implicated in exacerbating and/or causing many disease states in which massive neutrophil infiltration into sites of inlammation or injury (e.g., ischemia) is mediated chemotactic nature of IL-8, including, but not limited to, the following: asthma, inflammatory bowl disease, psoriasis, adult respiratory distress syndrome, cardiac and renal reperfusion injury, thrombosis and glomerulonephritis. In addition to the chemotaxis effect on neutrophils, IL-8 has also has ability to activate neutrophils. Thus, reduction in IL-8 levels may lead to diminished neutrophil infiltration.

Few prior art reference which disclose the closest pyrimidine compounds are given here:

i) U.S. Pat. Nos. 6,420,385 and 6,410,729 discloses novel compounds of formula (IIa)

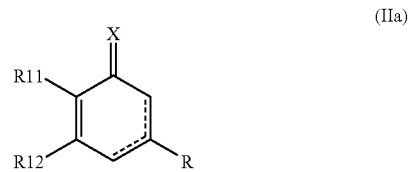

(IIa)

wherein

represents

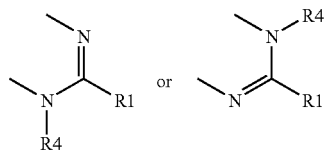

X is O, S or NR$_5$; R$_1$ and R$_2$ each independently represent —Y or -Z-Y, and R$_3$ and R$_4$ each independently -Z-Y or R$_3$ is a hydrogen radical; provided that R$_4$ is other than a substituted-aryl, (substituted-aryl)methyl or (substituted-aryl)ethyl radical; wherein each Z is independently optionally substituted alkyl, alkenyl, alkynyl, heterocyclyl, aryl or heteroaryl; Y is independently a hydrogen; halo, cyano, nitro, etc., R$_5$ is independently a hydrogen, optionally substituted alkyl, alkenyl, alkynyl etc., R$_{11}$ and R$_{12}$ are each independently represent optionally substituted aryl or heteroaryl.

An example of these compounds is shown in formula (IIb)

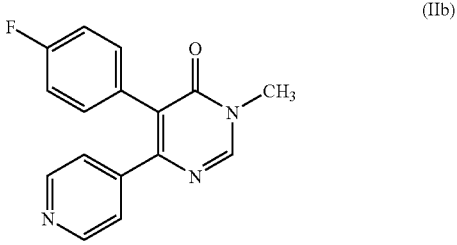

(IIb)

ii) DE 2142317 discloses hypnotic uracil derivatives of formula (IIc)

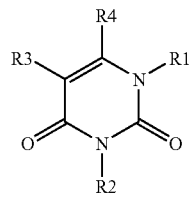

wherein $R_1$ is H, alkyl, alkenyl, dialkylaminoalkyl, or aralkyl; $R_2$ is H, alkyl, aryl, or halogen; $R_3$ is alkyl, alkenyl, cycloalkyl, aralkyl, aralkenyl, or aryl, $R_4$ is alkyl, alkenyl, cycloalkyl, aralkyl, aryl, etc.

An example of these compounds is shown in formula (IId)

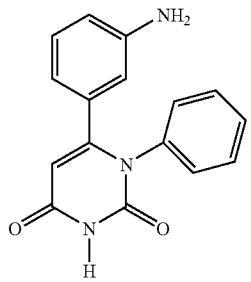

OBJECTIVE OF THE INVENTION

We have focused our research to identify selective COX-2 and COX-3 inhibitors, which are devoid of any side effects normally associated with anti-inflammatory agents. Our sustained efforts have resulted in novel pyrimidinedione derivatives of the formula (I). The derivatives may be useful in the treatment of inflammation and immunological diseases. Particularly the compound of the present invention are useful for the treatment of inflammation and immunological diseases those mediated by cytokines such as TNF-α, IL-1, IL-6, IL-1β, IL-8 and cyclooxygenase such as COX-2 and COX-3. The compound of the present invention are also useful for the treatment of rheumatoid arthritis; osteoporosis; multiple myeloma; uveititis; acute and chronic myelogenous leukemia; ischemic heart disease; atherosclerosis; cancer; ischemic-induced cell damage; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; type I and type II diabetes; bone resorption diseases; ischemia reperfusion injury; atherosclerosis; brain trauma; multiple sclerosis; cerebral malaria; sepsis; septic shock; toxic shock syndrome; fever, and myalgias due to infection; and diseases mediated by HIV-1; HIV-2; HIV-3; cytomegalovirus (CMV); influenza; adenovirus; the herpes viruses (including HSV-1, HSV-2) and herpes zoster viruses.

SUMMARY OF THE INVENTION

Accordingly, the present invention relates to novel pyrimidinedione derivatives of the formula (I)

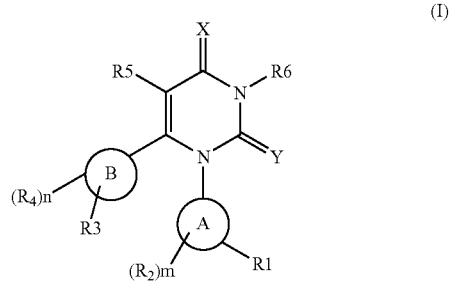

their derivatives, their analogs, their tautomeric forms, their stereoisomers, their polymorphs, their solvates, their pharmaceutically acceptable salts and their pharmaceutically acceptable compositions, wherein X and Y may be same or different and independently represent oxygen, sulfur or NR, wherein R represents hydrogen, hydroxyl, acyl, alkyl, alkoxy, aryl, amino, hydroxylamino, alkylamino, arylamino, acylamino, alkoxyamino group; the rings represented by A and B are selected from aryl or heteroaryl; $R^1$ and $R^3$ are different and represent hydrogen, $SR^7$, wherein $R^7$ represents alkyl or aryl; $S(O)_pR^8$, wherein $R^8$ represents alkyl, amino or aryl group and p represents an integer of 1 or 2; $R^2$ and $R^4$ may be same or different and independently represent hydrogen, halogen, hydroxyl, nitro, cyano, azido, nitroso, amino, formyl, alkyl, haloalkyl, acyl, alkoxy, monoalkylamino, dialkylamino, acylamino, alkoxycarbonyl, alkylsulfonyl, alkylsulfinyl, alkylsulfanyl, sulfamoyl, alkoxyalkyl groups or carboxylic acids or its derivatives; $R^5$ and $R^6$ may be same or different and independently represent hydrogen, halogen, hydroxyl, formyl, cyano, nitro, nitroso, amino, alkyl, acyl, monoalkylamino, dialkylamino, arylamino, acylamino, alkoxyalkyl or $COR^9$, wherein $R^9$ represents hydroxyl, amino, halogen, alkoxy, aryloxy, monoalkylamino, dialkylamino, arylamino groups; m is an integer and is in the range of 0 to 2; n is an integer and is in the range of 0 to 2.

DETAILED DESCRIPTION OF THE INVENTION

Suitable ring systems represented by A and B are selected from phenyl, naphthyl, pyrrolidinyl, morpholinyl, thiomorpholinyl, piperidinyl, piperazinyl, pyridyl, thienyl, furyl, pyrrolyl, oxazolyl, thiazolyl, imidazolyl, pyrazolyl, oxadiazolyl, thiadiazolyl, tetrazolyl, pyrimidinyl, benzopyranyl, benzofuranyl, benzimidazolyl, benzoxazolyl, benzothiazolyl, benzopyrolyl, benzoxadiazolyl, benzothiadiazolyl, quinolinyl, isoquinolinyl, benzothienyl, benzofuranyl, indolyl and the like.

Suitable groups represented by $R^1$ and $R^3$ are selected from hydrogen, $SR^7$ or $S(O)_pR^8$.

Suitable groups represented by $R^2$ and $R^4$ are selected from hydrogen, halogen atom such as fluorine, chlorine, bromine, iodine; hydroxyl, nitro, cyano, azido, nitroso, amino, formyl, linear or branched $(C_1-C_6)$alkyl group, such as methyl, ethyl, n-propyl, isopropyl, n-butyl, isobutyl, t-butyl, n-pentyl, isopentyl, hexyl and the like; haloalkyl such as chloromethyl, chloroethyl, trifluoromethyl, trifluoroethyl, dichloromethyl, dichloroethyl and the like; acyl group such as —C(=O)CH$_3$, —C(=O)C$_2$H$_5$, —C(=O)C$_3$H$_7$, —C(=O)C$_6$H$_{13}$, —C(=S)CH$_3$, —C(=S)C$_2$H$_5$, —C(=S)C$_3$H$_7$, —C(=S)C$_6$H$_{13}$, benzoyl; linear or branched (C$_1$-C$_6$)alkoxy group, such as methoxy, ethoxy, n-propoxy, isopropoxy and the like; monoalkylamino group such as NHCH$_3$, NHC$_2$H$_5$, NHC$_3$H$_7$, NHC$_6$H$_{13}$, and the like; dialkylamino group such as N(CH$_3$)$_2$, NCH$_3$(C$_2$H$_5$), N(C$_2$H$_5$)$_2$ and the like; acylamino group such as NHC(=O)CH$_3$, NHC(=O)C$_2$H$_5$, NHC(=O)C$_3$H$_7$, NHC(=O)C$_6$H$_{13}$, and the like; alkoxycarbonyl group such as methoxycarbonyl, ethoxycarbonyl, n-propoxycarbonyl, iso-propoxycarbonyl and the like; alkylsulfonyl group such as methylsulfonyl, ethylsulfonyl, n-propylsulfonyl, iso-propylsulfonyl and the like; alkylsulfinyl group such as methylsulfinyl, ethylsulfinyl, n-propylsulfinyl, iso-propylsulfinyl and the like; alkylthio group such as methylthio, ethylthio, n-propylthio, iso-propylthio and the like; sulfamoyl, alkoxyalkyl group such as methoxymethyl, ethoxymethyl, methoxyethyl, ethoxyethyl and the like; carboxylic acid or its derivatives such as esters, amides and acid halides.

Suitable groups represented by R$^5$ and R$^6$ are selected from hydrogen, halogen atom such as chlorine, fluorine, bromine or iodine; hydroxyl, formyl, cyano, nitro, nitroso, amino, linear or branched (C$_1$-C$_6$) alkyl group, such as methyl, ethyl, n-propyl, isopropyl, n-butyl, isobutyl, t-butyl, n-pentyl, isopentyl, hexyl and the like; acyl group such as C(=O)CH$_3$, —C(=O)C$_2$H$_5$, —C(=O)C$_3$H$_7$, —C(=O)C$_6$H$_{13}$, —C(=S)CH$_3$, —C(=S)C$_2$H$_5$, —C(=S)C$_3$H$_7$, —C(=S)C$_6$H$_{13}$, benzoyl; monoalkylamino group such as —NHCH$_3$, —NHC$_2$H$_5$, —NHC$_3$H$_7$, —NHC$_6$H$_{13}$, and the like; dialkylamino group such as —N(CH$_3$)$_2$, —NCH$_3$(C$_2$H$_5$), —N(C$_2$H$_5$)$_2$ and the like; arylamino such as phenyl amino, naphthyl amino and the like acylamino group such as —NHC(=O)CH$_3$, —NHC(=O)C$_2$H$_5$, —NHC(=O)C$_3$H$_7$, —NHC(=O)C$_6$H$_{13}$, and the like; alkoxyalkyl groups such as methoxymethyl, ethoxymethyl, methoxyethyl, ethoxyethyl and the like; or COR$^9$.

Suitable groups represented by R$^9$ are selected from hydroxy, amino, halogen, linear or branched (C$_1$-C$_6$) alkoxy group, such as methoxy, ethoxy, n-propoxy, isopropoxy and the like; aryloxy group such as phenoxy, napthoxy and the like; monoalkylamino group such as NHCH$_3$, NHC$_2$H$_5$, NHC$_3$H$_7$, NHC$_6$H$_{13}$, and the like, which may be substituted; dialkylamino group such as N(CH$_3$)$_2$, NCH$_3$(C$_2$H$_5$), N(C$_2$H$_5$)$_2$ and the like; arylamino such as phenyl amino, naphthyl amino and the like.

Suitable groups represented by R$^7$ are selected from linear or branched (C$_1$-C$_6$)alkyl group, such as methyl, ethyl, n-propyl, isopropyl, n-butyl, isobutyl, t-butyl, n-pentyl, isopentyl, hexyl and the like; aryl group such as phenyl or naphthyl.

Suitable groups represented by R$^8$ are selected from amino, linear or branched (C$_1$-C$_6$) alkyl group, such as methyl, ethyl, n-propyl, isopropyl, n-butyl, isobutyl, t-butyl, n-pentyl, isopentyl, hexyl and the like; aryl group such as phenyl or naphthyl.

Suitable groups represented by R are selected from hydrogen, hydroxy, amino, hydroxylamino, linear or branched (C$_1$-C$_6$)alkyl group, such as methyl, ethyl, n-propyl, isopropyl, n-butyl, isobutyl, t-butyl, n-pentyl, isopentyl, hexyl and the like; linear or branched (C$_1$-C$_6$) alkoxy group, such as methoxy, ethoxy, n-propoxy, isopropoxy and the like; aryl group such as phenyl, naphthyl and the like; acyl group such as —C(=O)CH$_3$, —C(=O)C$_2$H$_5$, —C(=O)C$_3$H$_7$, —C(=O)C$_6$H$_{13}$, —C(=S)CH$_3$, —C(=S)C$_2$H$_5$, —C(=S)C$_3$H$_7$, —C(=S)C$_6$H$_{13}$, benzoyl; aryl group such as phenyl or naphthyl; alkylamino group such as NHCH$_3$, NHC$_2$H$_5$, NHC$_3$H$_7$, NHC$_6$H$_{13}$, N(CH$_3$)$_2$, NCH$_3$(C$_2$H$_5$), N(C$_2$H$_5$)$_2$ and the like; acylamino group such as NHC(=O)CH$_3$, NHC(=O)C$_2$H$_5$, NHC(=O)C$_3$H$_7$, NHC(=O)C$_6$H$_{13}$, and the like; arylamino such as phenyl amino, naphthyl amino and the like; alkoxyamino such as methoxyamino, ethoxyamino, propoxy amino and the like.

m and n are integers ranging from 0-2.

Pharmaceutically acceptable salts of the present invention include alkali metal salts like Li, Na, and K salts, alkaline earth metal salts like Ca and Mg salts, salts of organic bases such as diethanolamine, α-phenylethylamine, benzylamine, piperidine, morpholine, pyridine, hydroxyethylpyrrolidine, hydroxyethylpiperidine, guanidine, choline and the like, ammonium or substituted ammonium salts, aluminum salts. Salts also include amino acid salts such as glycine, alanine, cystine, cysteine, lysine, arginine, phenylalanine etc. Salts may include acid addition salts where appropriate which are, sulphates, nitrates, phosphates, perchlorates, borates, hydrohalides, acetates, tartrates, maleates, citrates, succinates, palmoates, methanesulphonates, tosylates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

Representative compounds according to the present invention include:

1-(4-Methylsulfanyl-phenyl)-6-phenyl-pyrimidin-2,4-(1H)-dione;

6-(4-Methylphenyl)-1-(4-methylsulfanyl-phenyl)-pyrimidin-2,4-(1H)-dione;

6-(4-Ethylphenyl)-1-(4-methylsulfanyl-phenyl)-pyrimidin-2,4-(1H)-dione;

1-(4-Methylphenyl)-6-(4-methylsulfanyl-phenyl)-pyrimidin-2,4-(1H)-dione;

1-(4-Bromophenyl)-6-(4-methylsulfanyl-phenyl)-pyrimidin-2,4-(1H)-dione;

6-(4-Chlorophenyl)-1-(4-methylsulfanyl-phenyl)-pyrimidin-2,4-(1H)-dione;

6-(4-Chloro-3-methylphenyl)-1-(4-methylsulfanyl-phenyl)-pyrimidin-2,4-(1H)-dione;

6-(3-Chloro-4-methylphenyl)-1-(4-methylsulfanyl-phenyl)-pyrimidin-2,4-(1H)-dione;

6-(4-Fluoro-3-methylphenyl)-1-(4-methylsulfanyl-phenyl)-pyrimidin-2,4-(1H)-dione;

6-(4-Fluorophenyl)-1-(4-methylsulfanyl-phenyl)-pyrimidin-2,4-(1H)-dione;

6-(4-Methylsulfanyl-phenyl)-1-phenyl-pyrimidin-2,4-(1H)-dione;

6-(4-Methylphenyl)-1-(3-chloro-4-methylsulfonyl-phenyl)-pyrimidin-2,4-(1H)-dione;

6-(4-Methoxy-3-methylphenyl)-1-(4-methylsulfonyl-phenyl)-pyrimidin-2,4-(1H)-dione;

6-(4-Methylphenyl)-1-(4-methylsulfonyl-phenyl)-pyrimidin-2,4-(1H)-dione;

6-(4-Ethylphenyl)-1-(4-methylsulfonyl-phenyl)-pyrimidin-2,4-(1H)-dione;

6-(4-Chlorophenyl)-1-(4-methylsulfonyl-phenyl)-pyrimidin-2,4-(1H)-dione;

6-(4-Chloro-3-methylphenyl)-1-(4-methylsulfonyl-phenyl)-pyrimidin-2,4-(1H)-dione;

6-(4-Chlorophenyl)-1-(3-methoxy-4-methylsulfonyl-phenyl)-pyrimidin-2,4-(1H)-dione;

6-(3-Chloro-4-methylphenyl)-1-(4-methylsulfonyl-phenyl)-pyrimidin-2,4-(1H)-dione;

6-(4-Fluorophenyl)-1-(4-methylsulfonyl-phenyl)-pyrimidin-2,4-(1H)-dione;

1-(4-Methylsulfonyl-phenyl)-6-phenyl-pyrimidin-2,4-(1H)-dione;

1-(4-Methylsulfanyl-phenyl)-6-(pyridin-2-yl)-pyrimidin-2,4-(1H)-dione;

6-(4-Methylpyridin-2-yl)-1-(4-methylsulfanyl-phenyl)-pyrimidin-2,4-(1H)-dione;

6-(4-Chloropyridin-2-yl)-1-(4-methylsulfanyl-phenyl)-pyrimidin-2,4-(1H)-dione;

6-(4-Methylsulfanyl-phenyl)-1-(pyridin-2-yl)-pyrimidin-2,4-(1H)-dione;

1-(4-Methylsulfonyl-phenyl)-6-(pyridin-2-yl)-pyrimidin-2,4-(1H)-dione;

6-(4-Methylpyridin-2-yl)-1-(4-methylsulfonyl-phenyl)-pyrimidin-2,4-(1H)-dione;

6-(4-Chloropyridin-2-yl)-1-(4-methylsulfonyl-phenyl)-pyrimidin-2,4-(1H)-dione;

4-(2,4-Dioxo-6-(4-methylphenyl)-3,4-dihydro-2H-pyrimidin-1-yl)-benzenesulfonamide;

4-(2,4-Dioxo-6-phenyl-3,4-dihydro-2H-pyrimidin-1-yl)-benzenesulfonamide;

4-[6-(4-Bromo-phenyl)-2,4-dioxo-3,4-dihydro-2H-pyrimidin-1-yl]-benzenesulfonamide;

4-(2,6-Dioxo-3-phenyl-1,2,3,6-tetrahydro-pyrimidin-4-yl)-benzenesulfonamide;

4-(2,6-Dioxo-3-(4-methylsulfanyl-phenyl)-1,2,3,6-tetrahydro-pyrimidin-4-yl)-benzenesulfonamide and 4-[3-(4-Chloro-phenyl)-2,6-dioxo-1,2,3,6-tetrahydro-pyrimidin-4-yl]-benzenesulfonamide.

According to yet another embodiment of the present invention, there is provided a process for the preparation of novel pyrimidinedione derivatives of the formula (I) wherein all symbols are as defined above, as shown in scheme I below:

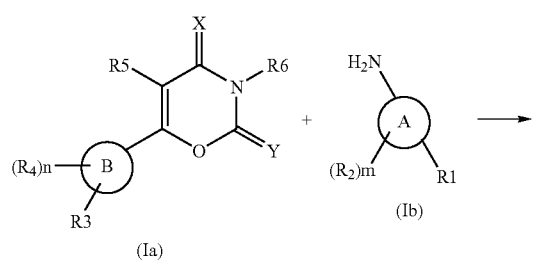

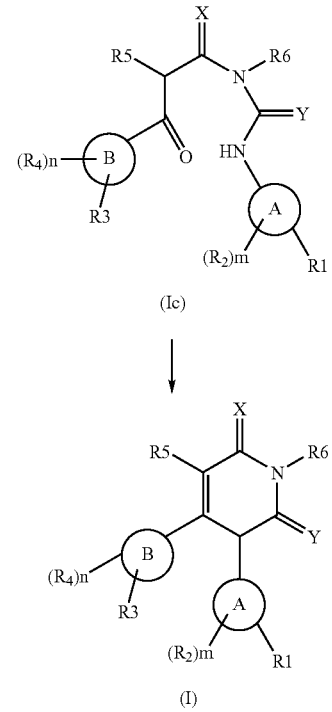

The reaction of compound of formula (Ia) with (Ib) to produce compound of formula (Ic) may be carried out in the presence of solvents such as toluene, xylene, tetrahydrofuran, dioxane, chloroform, dichloromethane, dichloroethane, o-dichlorobenzene, acetone, ethylacetate, acetonitrile, N,N-dimethylformamide, dimethylsulfoxide, ethanol, methanol, isopropylalcohol, tert-butylalcohol, acetic acid, propionic acid and the like or a mixture thereof. The condensation may be carried out under acidic conditions using mineral or organic acids or basic conditions using carbonates, bicarbonates, hydrides, hydroxides, alkyls and alkoxides of alkali metals and alkaline earth metals. The reaction may be carried out by using phase transfer catalysts viz. triethylbenzylammonium chloride, tetrabutylammonium bromide, tetrabutylammonium hydrogensulphate, tricaprylylmethylammonium chloride (aliquat 336) and the like. The reaction may be carried out at a temperature in the range of 50° C. to reflux temperature for period in the range of 2 to 12 h.

The cyclization of compound of formula (Ic) to obtain compound of formula (I) may be carried out in the presence of solvents such as toluene, xylene, tetrahydrofuran, dioxane, chloroform, dichloromethane, dichloroethane, o-dichlorobenzene, acetone, ethylacetate, acetonitrile, N,N-dimethylformamide, dimethylsulfoxide, ethanol, methanol, isopropylalcohol, tert-butylalcohol, acetic acid, propionic acid and the like or a mixture thereof. The cyclization is carried out under acidic conditions using mineral or organic acids or basic conditions using carbonates, bicarbonates, hydrides, alkyls and alkoxides of alkali metals and alkaline earth metals. The reaction may be carried out using phase transfer catalysts viz. triethylbenzylammonium chloride, tetrabutylammonium bromide, tetrabutylammonium hydrogensulphate, tricaprylylmethylammonium chloride (aliquat 336) and the like. The reaction may be carried out at a temperature in the range of 50° C. to reflux temperature for period in the range of 2 to 12 h.

In yet another embodiment of the present invention, there is provided a process for the preparation of novel pyrimidinedione derivatives of the formula (I) wherein either of $R^1$ and $R^3$ represent $S(O)_pR^8$, wherein $R^8$ represents amino group and p represents an integer of 1 or 2 and all other symbols are as defined earlier, which comprises reacting compound of formula (Id) wherein all symbols are as defined earlier

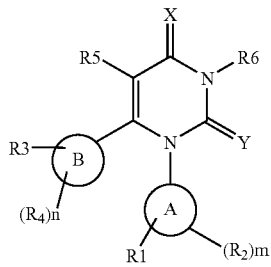

(Id)

wherein any one of $R^1$ and $R^3$ represent hydrogen with chlorosulfonic acid and ammonia.

The reaction of compound of formula (Id) with chlorosulfonic acid and ammonia may be carried out in the presence of solvents such as acetic acid, dichloromethane, acetone, tetrahydrofuran, dioxane, ethyl acetate, chloroform, water, an alcohol and the like or a mixture thereof. The reaction may be carried out at a temperature in the range of 50° C. to reflux temperature for period in the range of 2 to 12 h.

According to yet another embodiment of the present invention there is provided a process for the conversion of novel pyrimidinedione derivatives of the formula (I) wherein any of the groups $R^1$ or $R^3$ represent $SR^7$, wherein $R^7$ represents alkyl or aryl to novel pyrimidinedione derivatives of the formula (I) wherein any of the groups $R^1$ or $R^3$ represent $S(O)_p R^8$, where p represents 1 or 2 and $R^8$ represents alkyl or aryl; by using suitable oxidizing agent. The oxidizing agent may be selected from potassium peroxymonosulfate (Oxone), hydrogen peroxide, tert-butylperoxide, Jones reagent, peracid [e.g peracetic acid, perbenzoic acid, m-chloroperbenzoic acid etc], chromic acid, potassium permanganate, alkali metal periodate [e.g sodium periodate, etc], magnesium mono peroxypthalate, osmium tetroxide/N-methylmorpholine-N-oxide, sodium tungstate, and the like. The oxidation is usually carried out in a solvent which does not adversely influence the reaction such as acetic acid, dichloromethane, acetone, ethyl acetate, chloroform, water, alcohol [eg. methanol, ethanol, etc.], a mixture thereof or the like. The reaction temperature is usually carried out under cooling to refluxing conditions.

According to yet another embodiment of the present invention there is provided a process for the conversion of novel pyrimidinedione derivatives of the formula (I) wherein $R^1$ or $R^3$ represent $S(O)_pR^8$, where p is 1 or 2, $R^8$ represents alkyl or aryl to novel pyrimidinedione derivatives of the formula (I) wherein $R^1$ or $R^3$ represent $S(O)_pR^8$, where p is 1 or 2, $R^8$ represents amino by using the procedure described in the literature (Huang et al Tetrahedron Lett. 39, 7201, 1994).

In yet another embodiment of the present invention, there is provided a novel intermediate of formula (Ia)

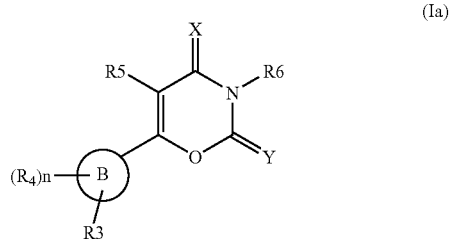

(Ia)

their derivatives, their analogs, their tautomeric forms, their stereoisomers, their polymorphs, and their pharmaceutically acceptable salts, wherein X and Y may be same or different and independently represent oxygen, sulfur or NR, wherein R represents hydrogen, hydroxyl, acyl, alkyl, alkoxy, aryl, amino, hydroxylamino, alkylamino, arylamino, acylamino, alkoxyamino group; the ring represented by B is selected from aryl or heteroaryl; $R^3$ represents $SR^7$, wherein $R^7$ represents alkyl or aryl; $S(O)_pR^8$, wherein $R^8$ represents alkyl, amino or aryl group and p represents an integer of 1 or 2; $R^4$ represents hydrogen, halogen, hydroxyl, nitro, cyano, azido, nitroso, amino, formyl, alkyl, haloalkyl, acyl, alkoxy, monoalkylamino, dialkylamino, acylamino, alkoxycarbonyl, alkylsulfonyl, alkylsulfinyl, alkylthio, sulfamoyl, alkoxyalkyl groups or carboxylic acids or its derivatives; $R^5$ and $R^6$ may be same or different and independently represent hydrogen, halogen, hydroxyl, formyl, cyano, nitroso, nitro, amino, alkyl, acyl, monoalkylamino, dialkylamino, arylamino, acylamino, alkoxyalkyl or $COR^9$, wherein $R^9$ represents hydroxyl, amino, halogen, alkoxy, aryloxy, monoalkylamino, dialkylamino, arylamino, groups; n is an integer and represents 0 to 2.

In yet another embodiment of the present invention, there is provided a process for the preparation of compound of formula (Ia) as shown in scheme 2 below.

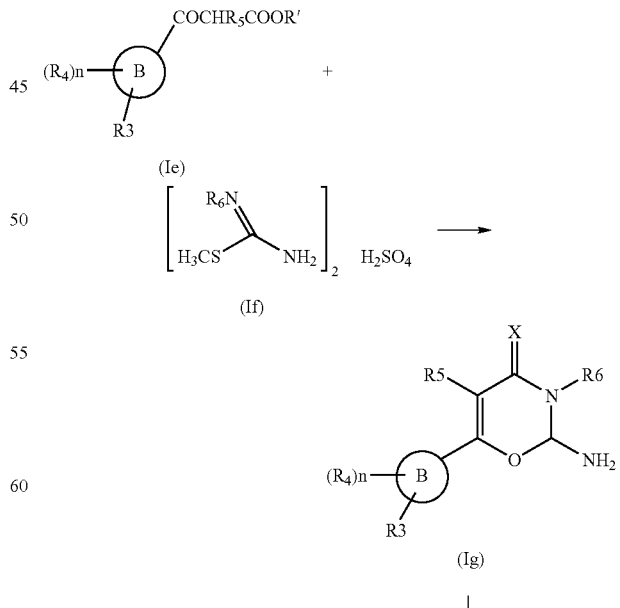

-continued

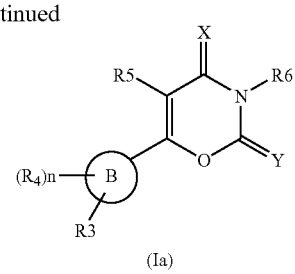

(Ia)

The reaction of compound of formula (Ie) wherein R' represents alkyl group and all other symbols are as defined above with (If) to produce compound of formula (Ig) may be carried out in the presence of solvents such as toluene, xylene, tetrahydrofuran, dioxane, chloroform, dichloromethane, dichloroethane, o-dichlorobenzene, acetone, ethylacetate, acetonitrile, N,N-dimethylform amide, dimethylsulfoxide, ethanol, methanol, isopropylalcohol, tert-butylalcohol, acetic acid, propionic acid and the like or a mixture thereof. The reaction may be carried out in the presence of base such as sodium hydroxide, potassium hydroxide, sodium bicarbonate, sodium carbonate and the like. The reaction may be carried out at a temperature in the range of 10 to 80° C. for period in the range of 4 to 24 h.

The conversion of compound of formula (Ig) to obtain compound of formula (Ia) may be carried out in the presence of acids such as hydrochloric acid, sulfuric acid, acetic acid, nitrous acid and the like.

In yet another embodiment of the present invention, there is provided a novel intermediate of formula (Ic)

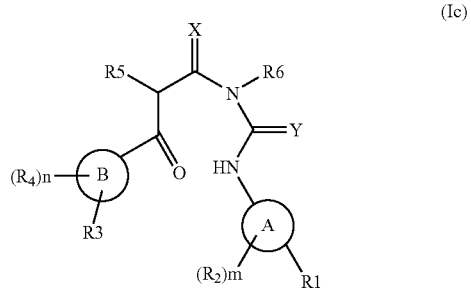

(Ic)

their derivatives, their analogs, their tautomeric forms, their stereoisomers, their polymorphs, and their pharmaceutically acceptable salts, wherein X and Y may be same or different and independently represent oxygen, sulfur or NR, wherein R represents hydrogen, hydroxyl, acyl, alkyl, alkoxy, aryl, amino, hydroxylamino, alkylamino, arylamino, acylamino, alkoxyamino group; the rings represented by A and B are selected from aryl or heteroaryl; $R^1$ and $R^3$ are different and represent hydrogen, $SR^7$, wherein $R^7$ represents alkyl or aryl; $S(O)_pR^8$, wherein $R^8$ represents alkyl, amino or aryl group and p represents an integer of 1 or 2; $R^2$ and $R^4$ may be same or different and independently represent hydrogen, halogen, hydroxyl, nitro, cyano, azido, nitroso, amino, formyl, alkyl, haloalkyl, acyl, alkoxy, monoalkylamino, dialkylamino, acylamino, alkoxycarbonyl, alkylsulfonyl, alkylsulfinyl, alkylthio, sulfamoyl, alkoxyalkyl groups or carboxylic acids or its derivatives; $R^5$ and $R^6$ may be same or different and independently represent hydrogen, halogen, hydroxyl, formyl, cyano, nitro, nitroso, amino, alkyl, acyl, monoalkylamino, dialkylamino, arylamino, acylamino, alkoxyalkyl or $COR^9$, wherein $R^9$ represents hydroxy, amino, halogen, alkoxy, aryloxy, monoalkylamino, dialkylamino, arylamino, groups; m is an integer and is in the range of 0 to 2; n is an integer and is in the range of 0 to 2.

It is appreciated that in any of the above-mentioned reactions, any reactive group in the substrate molecule may be protected according to conventional chemical practice. Suitable protecting groups in any of the above-mentioned reactions are those used conventionally in the art. The methods of formation and removal of such protecting groups are those conventional methods appropriate to the molecule being protected.

The pharmaceutically acceptable salts are prepared by reacting the compound of formula (I) with 1 to 4 equivalents of a base such as sodium hydroxide, sodium methoxide, sodium hydride, potassium t-butoxide, calcium hydroxide, magnesium hydroxide and the like, in solvents like ether, tetrahydrofuran, methanol, t-butanol, dioxane, isopropanol, ethanol etc. Mixture of solvents may be used. Organic bases such as diethanolamine, α-phenylethylamine, benzylamine, piperidine, morpholine, pyridine, hydroxyethylpyrrolidine, hydroxyethylpiperidine, guanidine, choline and the like, ammonium or substituted ammonium salts, aluminum salts. Amino acid such as glycine, alanine, cystine, cysteine, lysine, arginine, phenylalanine, etc may be used for the preparation of amino acid salts. Alternatively, acid addition salts wherever applicable are prepared by the treatment with acids such as hydrochloric acid, hydrobromic acid, nitric acid, sulfuric acid, phosphoric acid, p-toluenesulphonic acid, methanesulfonic acid, acetic acid, citric acid, maleic acid, salicylic acid, hydroxynaphthoic acid, ascorbic acid, palmitic acid, succinic acid, benzoic acid, benzenesulfonic acid, tartaric acid and in solvents like ethyl acetate, ether, alcohols, acetone, tetrahydrofuran, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid, and the like wherever applicable or chiral bases such as brucine, cinchona alkaloids and their derivatives and the like. Commonly used methods are compiled by Jaques et al in "Enantiomers, Racemates and Resolution" (Wiley Interscience, 1981). More specifically the compound of formula (I) may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula (I) may be prepared by hydrolysing the pure diastereomeric amide.

Various polymorphs of compound of general formula (I) forming part of this invention may be prepared by crystallization of compound of formula (I) under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffraction or such other techniques.

Pharmaceutically acceptable solvates of the compounds of formula (I) forming part of this invention may be prepared by conventional methods such as dissolving the compounds of formula (I) in solvents such as water, methanol, ethanol, mixture of solvents such as acetone:water, dioxane:water, N,N-dimethylformamide:water and the like, preferably water and recrystallizing by using different crystallization techniques.

The novel pyrimidinedione derivatives of the present invention are useful for the treatment of inflammation and immunological diseases. Particularly the compound of the present invention are useful for the treatment of inflammation and immunological diseases those mediated by cytokines such as TNF-α, IL-1, IL-6, IL-1β, IL-8 and cyclooxygenase such as COX-2 and COX-3. The compounds of the present invention are also useful for the treatment of rheumatoid arthritis; osteoporosis; multiple myeloma; uveititis; acute and chronic myelogenous leukemia; ischemic heart disease; atherosclerosis; cancer; ischemic-induced cell damage; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; type I and type II diabetes; bone resorption diseases; ischemia reperfusion injury; atherosclerosis; brain trauma; multiple sclerosis; cerebral malaria; sepsis; septic shock; toxic shock syndrome; fever and myalgias due to infection; and the diseases mediated by HIV-1; HIV-2; HIV-3; cytomegalovirus (CMV); influenza; adenovirus; the herpes viruses (including HSV-1, HSV-2) and herpes zoster viruses.

The compounds of the present invention also may possess analgesic properties and may be useful for the treatment of pain disorders, such as hyperalgesia due to excessive IL-1. The compounds of the present invention may also prevent the production of prostaglandins by inhibition of enzymes in the human arachidonic acid/prostaglandin pathway, including cyclooxygenase.

The pharmaceutically active compounds of this invention can be processed in accordance with conventional methods of pharmacy to produce medicinal agents for administration to patients, including humans and other mammals.

The present invention provides a pharmaceutical composition, containing the compounds of the general formula (I) as defined above, their derivatives, their analogs, their tautomeric forms, their stereoisomers, their polymorphs, their pharmaceutically acceptable hydrates and solvates in combination with the usual pharmaceutically employed carriers, diluents and the like, useful for the treatment of arthritis, pain, fever, psoriasis, allergic diseases, asthma, inflammatory bowel syndrome, gastro-intestinal ulcers, cardiovascular disorders including ischemic heart disease, atherosclerosis, cancer, ischemic-induced cell damage, particularly brain damage caused by stroke, other pathological disorders associated with free radicals. The pharmaceutical composition of the present invention are effective in the treatment of inflammation and immunological diseases, particularly those mediated by cytokines such as TNF-α, IL-1, IL-6, IL-8 and cyclooxygenase such as COX-2 and COX-3.

The pharmaceutical composition may be in the forms normally employed, such as tablets, capsules, powders, syrups, solutions, aerosols, suspensions and the like, may contain flavoring agents, sweeteners etc. in suitable solid or liquid carriers or diluents, or in suitable sterile media to form injectable solutions or suspensions. Such compositions typically contain from 1 to 20%, preferably 1 to 10% by weight of active compound, the remainder of the composition being pharmaceutically acceptable carriers, diluents or solvents.

The present invention is provided by the examples given below, which are provided by way of illustration only and should not be considered to limit the scope of the invention.

Preparation 1

Synthesis of ethyl (4-methyl)benzoylacetate

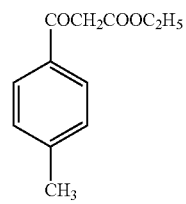

Sodium hydroxide solution (33%, 32.5 ml) was added to ethyl acetoacetate (97.5 g, 750 mmol) in a mixture of water (250 ml) and toluene (12 ml) at 0-5° C. under stirring (pH 11). After 30 minutes 4-methylbenzoylchloride (127.46 g, 825 mmol) and sodium hydroxide solution (33%, 135 ml) was added simultaneously over a period two hours. The reaction mixture was stirred for 15 minutes at 0° C. and for 1 hour at 35° C. Aqueous layer was separated, ammonium chloride (40 g) was added and stirred slowly over night. The reaction mixture was saturated with sodium chloride and extracted with ethyl acetate. The ethyl acetate extract was washed with water, dried over anhydrous sodium sulphate and concentrated to dryness in vacuum. The crude product thus obtained was purified by column chromatography to yield the title compound as viscous oil (54 g, 35%). MS m/z: 207.1 ($M^+$).

Preparation 2

Synthesis of ethyl (4-methyl)benzoylacetate

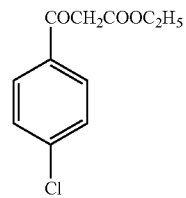

Ethyl acetoacetate (51.25 g, 390 mmol) was added dropwise to the stirred suspension of anhydrous magnesium chloride (37.54 g, 390 mmol) in dried dichloromethane (200 ml) over a period of 1 hour under argon atmosphere at 0° C. followed by pyridine (62.5 g, 788 mmol). After 15 minutes, 4-chlorobenzoylchloride (68.95 g, 394 mmol) was added dropwise and stirring was continued for 15 minutes at 0° C. and further stirred for 1.5 hours at 30° C. The resulting reaction mixture was neutralized with hydrochloric acid (6N, 235 ml) at 0-5° C., filtered and washed with water. The filtrate was extracted with diethylether (3×100 ml). The ether extract was washed with water, dried over anhydrous sodium sulphate and concentrated to dryness in vacuum. The obtained oil was taken in ammonium chloride (21 g in 200 ml water) solution containing ammonia (2 ml) and stirred at 30° C. for 20 minutes. The resulting solution was extracted with ethyl acetate (3×200 ml). Ethyl acetate extract was dried over anhydrous sodium sulphate, concentrated to yield the crude product, which was purified by column chromatography to yield the title compound as viscous oil (43 g, 48.2%). $^1$H-NMR (DMSO-$d_6$): δ 1.15-1.18 (t, 3H), 4.08-4.13 (q, 2H), 4.20 (s, 2H), 7.61-7.64 (d, 2H), 7.94-7.97 (d, 2H). MS m/z: 227.1 ($M^+$).

Preparation 3

Synthesis of ethyl (4-methylthio)benzoylacetate

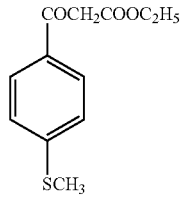

Lithium bis(trimethylsilyl)amide (20% in tetrahydrofuran, 203.6 ml, 217 mmol) was added dropwise to a stirred solution of 4-methylthioacetophenone (20.2 g, 121 mmol) in dried tetrahydrofuran (300 ml) at −20° C. and stirring was continued for 1 hour at −20° C. Ethylchloroformate (19.8 g, 182 mmol) was added dropwise to the stirred reaction mixture at −20° C. and stirring was continued for 3 hours. The reaction was quenched with saturated ammonium chloride solution and extracted with ethylacetate. The organic extract was washed with water, brine, dried over anhydrous sodium sulphate and concentrated to dryness in vacuum. The crude product thus obtained was purified by column chromatography to yield the title compound as viscous oil (16.45 g, 56.8%). $^1$H-NMR (DMSO-$d_6$): δ 1.15-1.19 (t, 3H), 2.54 (s, 3H), 4.07-4.11 (q, 2H), 4.13 (s, 2H), 7.36-7.39 (d, 2H), 7.85-7.88 (d, 2H). MS m/z: 239 ($M^+$).

Preparation 4

Synthesis of 2-amino-6-(4-methylphenyl)-1,3-oxazin-4-one

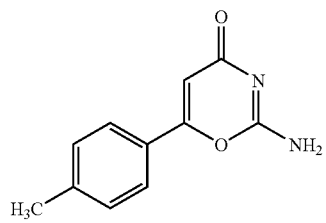

Potassium hydroxide (12.55 g, 224 mmol) was added to the vigorously stirred solution of methylthiopseudourea.$H_2SO_4$ (14.57 g, 52 mmol) in water (80 ml). Ethyl (4-methyl)benzoylacetate (20.0 g, 97 mmol) (obtained in preparation 1) was added to it and stirred at room temperature for 18 hours. The solid thus obtained was filtered, washed with water, ether and dried at 60° C. in vacuum to yield the title compound (1.85 g, 9.5%). $^1$H-NMR (DMSO-$d_6$): δ 2.37 (s, 3H), 6.46 (s, 1H), 7.33-7.35 (d, 2H), 7.76-7.78 (d, 2H), 7.91 (bs, 2H, $D_2O$ exchangeable). MS m/z: 203.1 ($M^+$).

Preparation 5

Synthesis of 2-amino-6-(4-chlorophenyl)-1,3-oxazin-4-one

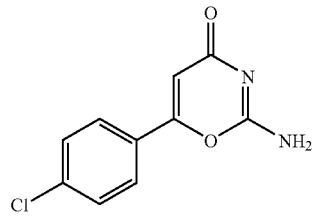

The title compound was prepared from ethyl(4-chloro) benzoylacetate (5.0 g, 22 mmol) (obtained in preparation 2) and methylthiopseudourea.$H_2SO_4$ (3.31 g, 12 mmol) by following the procedure described in preparation 4, (0.573 g, 11.6%). MS m/z: 223 ($M^+$).

Preparation 6

Synthesis of 2-amino-6-(4-methylsulfanyl-phenyl)-1,3-oxazin-4-one

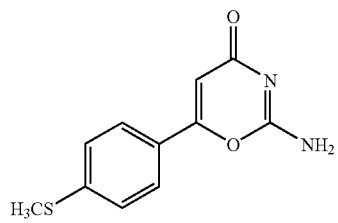

The title compound was prepared from ethyl(4-methylthiobenzoyl)acetate (16.447 g, 69 mmol) (obtained in preparation 3) and methylthiopseudourea.$H_2SO_4$ (10.56 g, 38 mmol) according to the procedure described in preparation 4, (1.82 g, 11.5%, mp 266-267° C.). $^1$H-NMR (DMSO-$d_6$): δ 2.53 (s, 3H), 6.48 (s, 1H), 7.37-7.39 (d, 2H), 7.79-7.81 (d, 2H), 7.92 (bs, 2H). MS m/z: 235 ($M^+$).

Preparation 7

Synthesis of 6-(4-methylphenyl)-2H-3,4-dihydro-1,3-oxazin-2,4-dione

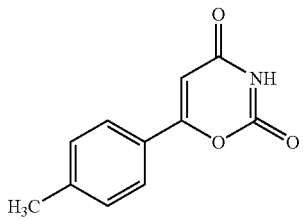

A suspension of 2-amino-6-(4-methylphenyl)-1,3-oxazin-4-one (1.0 g, 5 mmol) (obtained in preparation 4) in 10% hydrochloric acid (60 ml) was refluxed for 1 hr. The resulting suspension was cooled, filtered, washed with water and dried at 60° C. in vacuum for 8 hours to yield the title compound (0.32 g, 32%). $^1$H-NMR (DMSO-$d_6$): δ 2.38 (s, 3H), 6.65 (s, 1H), 7.35-7.37 (d, 2H), 7.79-7.81 (d, 2H), 11.89 (bs, 1H, $D_2O$ exchangeable). MS m/z: 203.1 ($M^+$).

Preparation 8

Synthesis of 6-(4-chlorophenyl)-2H-3,4-dihydro-1,3-oxazin-2,4-dione

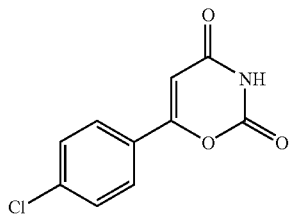

The title compound was prepared from 2-amino-6-(4-chlorophenyl)-1,3-oxazin-4-one (0.573 g, 2.6 mmol) (obtained in preparation 5) according to the procedure described in preparation 7 (0.57 g, 99%, mp 254-256° C). $^1$H-NMR (DMSO-$d_6$): δ 6.65 (s, 1H), 7.58-7.60 (d, 2H), 7.86-7.89 (d, 2H), 11.90 (bs, 1H, $D_2O$ exchangeable).

Preparation 9

Synthesis of 6-(4-methylsulfanyl-phenyl)-2H-3,4-dihydro-1,3-oxazin-2,4-dione

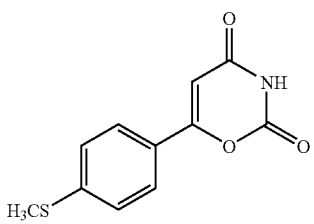

The title compound was prepared from 2-amino-6-(4-methylsulfanyl-phenyl)-1,3-oxazin-4-one (1.82 g, 7.8 mmol) (obtained in preparation 6) by following the procedure described in preparation 7 (0.78 g, 42.7%). $^1$H-NMR (DMSO-$d_6$): δ 2.53 (s, 3H), 6.67 (s, 1H), 7.37-7.40 (d, 2H), 7.81-7.83 (d, 2H), 11.89 (bs, 1H). MS m/z: 235 ($M^+$).

Preparation 10

Synthesis of N-(4-methylsulfanyl-phenyl)-[N'-1-(3-phenyl)-1,3-diketone]urea

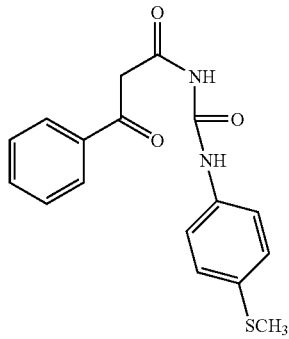

4-Methylthioaniline (3.36 g, 24 mmol) was added to a stirred suspension of 6-phenyl-2H-3,4-dihydro-1,3-oxazin-2,4-dione (0.189 g, 1 mmol) (synthesized according to the procedure given in Harvey I. Skulnick, Heterocylces, 23 (7), pp 1685, 1985) in ethanol (5 ml). The reaction mixture was refluxed for 4 hours, cooled at room temperature, filtered, washed with ethanol, ether, dried in vacuum at 60° C. for 5 hours to yield the title compound (0.1 g, 30.5%, mp 143-145° C.). $^1$H-NMR (DMSO-$d_6$): δ 2.45 (s, 3H), 4.28 (s, 1H), 7.23-7.27 (d, 2H), 7.47-7.59 (m, 4H), 7.67-7.69 (d, 1H), 7.96-7.98 (d, 2H). MS m/z: 329.2 ($M^+$).

Preparation 11

Synthesis of N-(4-methylsulfanyl-phenyl)-{N'-1-[3-(4-methyl)phenyl]-1,3-diketone}urea

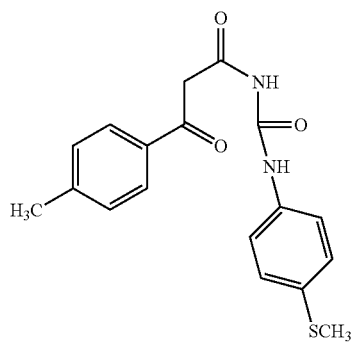

4-Methylthioaniline (0.636 g, 4.6 mmol) was added to the stirred suspension of 6-(4-methylphenyl)-2H-3,4-dihydro-1,3-oxazine-2,4-dione (0.310 g, 1.5 mmol) (obtained in preparation 7) in ethanol (10 ml). The reaction mixture was refluxed with stirring for 6 hours, cooled at room temperature, filtered, washed with ethanol followed by ether and dried in vacuum at 60° C. for five hours to yield the title compound (0.24 g, 46%, mp 234-237° C.). $^1$H-NMR (DMSO-$d_6$): δ 2.35

(s, 3H), 2.38 (s, 3H), 6.65 (s, 1H), 7.47-7.49 (d, 4H), 7.79-7.81 (d, 4H), 11.89 (bs, 1H). MS m/z: 343.1 (M⁺).

Preparation 12

Synthesis of N-(4-methylsulfanyl-phenyl)-{N'-1-[3-(4-chlorophenyl)]-1,3-diketone}urea

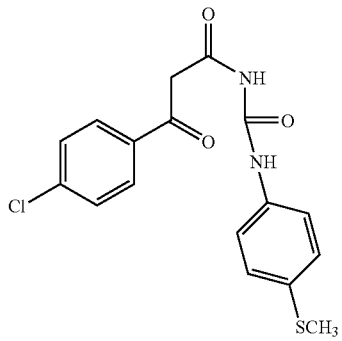

The title compound was prepared from 6-(4-chlorophenyl)-2H-3,4-dihydro-1,3-oxazin-2,4-dione (0.57 g, 2.5 mmol) (obtained in preparation 8) and 4-methylthioaniline (2.48 g, 17.8 mmol) according to the procedure described in preparation 11 (0.33 g, 35.7%). ¹H-NMR (DMSO-d₆): δ 2.41 (s, 3H), 6.64 (s, 1H), 7.10-7.19 (m, 4H), 7.25-7.33 (m, 4H), 11.59 (bs, 1H). MS m/z: 363 (M⁺).

Preparation 13

Synthesis of N-(4-methylphenyl)-{N'-1-[3-(4-methylsulfanyl-phenyl)]-1,3-diketone}urea

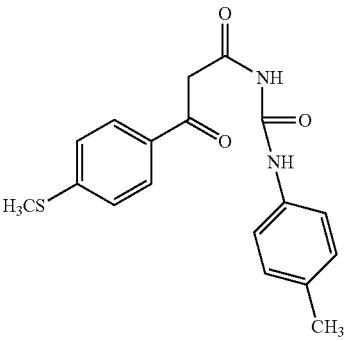

The title compound was prepared from 6-(4-methylsulfanyl-phenyl)-2H-3,4-dihydro-1,3-oxazin-2,4-dione (0.35 g, 1.5 mmol) (obtained in preparation 9) and 4-methylaniline (1.12 g, 10.4 mmol) according to the procedure described in preparation 11 (0.24 g, 47%). ¹H-NMR (DMSO-d₆): δ 2.26 (s, 3H), 2.53 (s, 3H), 4.22 (s, 1H), 7.12-7.14 (d, 2H), 7.38-7.42 (d, 4H), 7.87-7.89 (d, 2H). MS m/z: 343.1 (M⁺).

Preparation 14

Synthesis of N-(4-bromophenyl)-{N'-1-[3-(4-methylsulfanyl-phenyl)]-1,3-diketone}urea

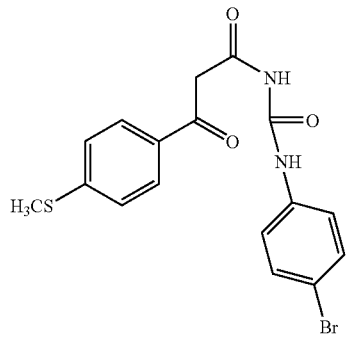

The title compound was prepared from 6-(4-methylsulfanyl-phenyl)-2H-3,4-dihydro-1,3-oxazin-2,4-dione (0.7 g, 2.99 mmol) (obtained in preparation 9) and 4-bromoaniline (3.6 g, 20 mmol) by following the procedure described in preparation 11 (0.445 g, 36.8%). ¹H-NMR (DMSO-d₆): δ 2.55 (s, 3H), 6.68 (s, 1H), 7.37-7.39 (d, 4H), 7.49 (s, 2H), 7.81-7.83 (d, 4H), 11.8 (bs, 1H). MS m/z: 407.2 (M⁺).

EXAMPLE 1

Synthesis of 1-(4-methylsulfanyl-phenyl)-6-phenyl-1H-pyrimidin-2,4-(1H)-dione

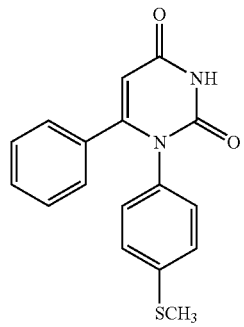

A mixture of N-(4-methylsulfanyl-phenyl)-[N'-1-(3-phenyl)-1,3-diketone]urea (0.1 g, 0.3 mmol) (obtained in preparation 10) and p-toluenesulfonic acid (0.057 g, 0.3 mmol) in toluene (10 ml) was refluxed with stirring for 4 hours. The reaction mixture was allowed to cool at room temperature, poured into water and extracted with ethylacetate. The ethylacetate extract was washed with water, dried over anhydrous sodium sulphate and concentrated to dryness under reduced pressure. The crude solid thus obtained was purified by column chromatography to yield the title compound (0.09 g, 95.2%, mp 239-242° C. (decomposed), purity 98.10% by HPLC). ¹H-NMR (DMSO-d₆): δ 2.39 (s, 3H), 5.63 (s, 1H), 7.07-7.10 (d, 2H), 7.14-7.17 (d, 2H), 7.22-7.24 (s, 5H), 11.54 (s, 1H). IR (KBr) cm⁻¹: 3188, 3040 (—NH—), 1720, 1681 (—C=O). MS m/z: 311.1 (M⁺).

EXAMPLE 2

Synthesis of 1-(4-methylsulfanyl-phenyl)-6-(4-methylphenyl)-1H-pyrimidin-2,4-(1H)-dione

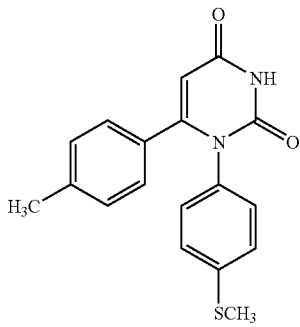

The title compound was prepared from N-(4-methylsulfanyl-phenyl)-{N'-1-[3-(4-methylphenyl)]-1,3-diketone}urea (0.24 g, 0.7 mmol) (obtained in preparation 11) and p-toluenesulfonic acid (0.134 g, 0.7 mmol) in toluene (10 ml) by refluxing for 2 hours and following the procedure described in example 1 (0.17 g, 74.9%, mp 235-238° C., purity 98.9% by HPLC). $^1$H-NMR (DMSO-d$_6$): δ 2.20 (s, 3H), 2.40 (s, 3H), 5.59 (s, 1H), 7.02-7.17 (m, 8H), 11.53 (bs, 1H). IR (KBr) cm$^{-1}$: 3180, 3051 (—NH—), 1693 (—C=O). MS m/z: 325.3 (M$^+$).

EXAMPLE 3

Synthesis of 1-(4-methylsulfanyl-phenyl)-6-(4-chlorophenyl)-1H-pyrimidin-2,4-(1H)-dione

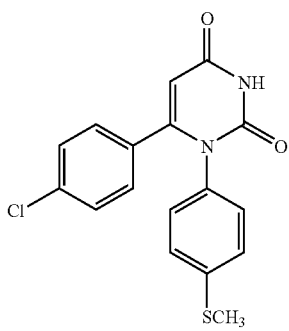

The title compound was prepared from N-(4-methylsulfanyl-phenyl)-{N'-1-[3-(4-chlorophenyl)]-1,3-diketone}urea (0.33 g, 0.91 mmol) (obtained in preparation 12) in toluene (30 ml) containing p-toluenesulfonic acid (0.294 g, 1.6 mmol) was refluxed for 9 hours by following the procedure described in example 1 (0.289 g, 92.2%, mp 249-251° C., purity 99.6% by HPLC). $^1$H-NMR (DMSO-d$_6$): δ 2.41 (s, 3H), 5.67 (s, 1H), 7.10-7.19 (m, 4H), 7.25-7.33 (m, 4H), 11.5 (bs, 1H). IR (KBr) cm$^{-1}$: 3178, 3054 (—NH—), 1691 (—C=O). MS m/z: 345 (M$^+$).

EXAMPLE 4

Synthesis of 1-(4-methylphenyl)-6-(4-methylsulfanyl-phenyl)-1H-pyrimidin-2,4-(1H)-dione

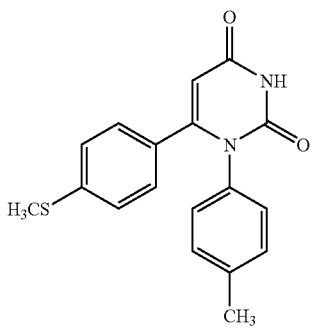

The title compound was prepared from N-(4-methylphenyl)-{N'-1-[3-(4-methylsulfanyl-phenyl)]-1,3-diketone}urea (0.24 g, 0.7 mmol) (obtained in preparation 13) and p-toluenesulfonic acid (0.134 g, 0.7 mmol) in toluene (10 ml) by refluxing for 4 hours and following the procedure described in example 1 (0.186 g, 82%, mp 266-268° C., purity 99.8% by HPLC). $^1$H-NMR (DMSO-d$_6$): δ 2.20 (s, 3H), 2.38 (s, 3H), 5.60 (s, 1H), 7.03-7.13 (m, 8H), 11.59 (bs, 1H, D$_2$O exchangeable). IR (KBr) cm$^{-1}$: 3335 (—NH—), 1683 (—C=O). MS m/z: 325.2 (M$^+$).

EXAMPLE 5

Synthesis of 1-(4-bromophenyl)-6-(4-methylsulfanyl-phenyl)-1H-pyrimidin-2,4-(1H)-dione

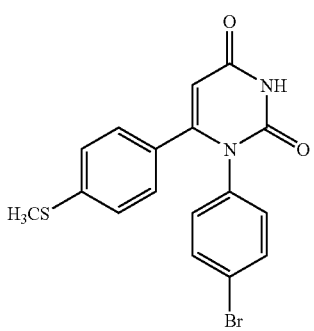

The title compound was prepared from N-(4-bromophenyl)-{N'-1-[3-(4-methylsulfanyl-phenyl)]-1,3-diketone}urea (0.430 g, 1.05 mmol) (obtained in preparation 14) in toluene (10 ml) containing p-toluenesulfonic acid (0.602 g, 3 mmol) was refluxed for 8 hours and following the procedure described in example 1 (0.151 g, 36.8%, mp 282-285° C., purity 97.8% by HPLC). $^1$H-NMR (DMSO-d$_6$): δ 2.55 (s, 3H), 5.68 (s, 1H), 7.08-7.01 (d, 2H), 7.15-7.17 (d, 2H), 7.20-7.22 (d, 2H), 7.48-7.50 (d, 2H), 11.58 (bs, 1H, D$_2$O exchangeable). IR (KBr) cm$^{-1}$: 3155 (—NH—), 3022, 1712 (—C=O). MS m/z: 389 (M$^+$).

EXAMPLE 6

Synthesis of 1-(4-methylsulfonyl-phenyl)-6-phenyl-pyrimidin-1H-pyrimidin-2,4-(1H)-dione

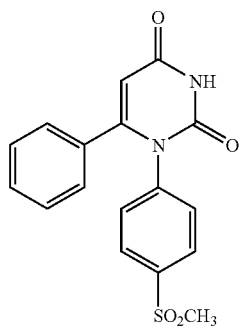

Oxone (1.189 g, 1.93 mmol) in water (5 ml) was added dropwise to a stirred suspension of 1-(4-methylsulfanyl-phenyl)-6-phenyl-1H-pyrimidin-2,4-(1H)-dione (0.2 g, 0.64 mmol) (obtained according to the procedure described in example 1) in methanol (10 ml) and stirring was continued for 3 hours at room temperature. Saturated sodium bicarbonate solution (20 ml) was added to the reaction mixture and extracted with ethylacetate. The ethylacetate extract was washed with water, brine, dried over anhydrous sodium sulphate and concentrated to dryness under reduced pressure. The crude solid thus obtained was purified by column chromatography to yield the title compound (0.117 g, 53.2%, mp 283-287° C. (decompose), purity 96.5% by HPLC). $^1$H-NMR (DMSO-$d_6$): δ 3.18 (s, 3H), 5.72 (s, 1H), 7.21-7.25 (s, 5H), 7.53-7.55 (d, 2H), 7.78-7.8 (d, 2H), 11.68 (bs, 1H). IR (KBr) cm$^{-1}$: 3033 (—NH—), 1719, 1684 (—C═O). MS m/z: 343.1 (M$^+$).

EXAMPLE 7

Synthesis of 6-(4-methylphenyl-1-(4methylsulfonyl-phenyl)-1H-pyrimidin-2,4-(1H)-dione

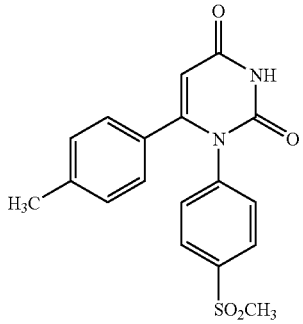

The title compound was prepared from 1-(4-methylsulfanyl-phenyl)-6-(4-methylphenyl)-1H-pyrimidin-2,4-(1H)-dione (0.3 g, 0.92 mmol) (obtained according to the procedure described in example 2) by following the procedure described in example 6 (0.244 g, 74.2%, mp 285-288° C., purity 99.4% by HPLC). $^1$H-NMR (DMSO-$d_6$): δ 2.19 (s, 3H), 3.20 (s, 3H), 5.68 (s, 1H), 7.03-7.05 (d, 2H), 7.05-7.09 (d, 2H), 7.53-7.55 (d, 2H), 7.80-7.82 (d, 2H), 11.65 (bs, 1H, $D_2O$ exchangeable). IR (KBr) cm$^{-1}$: 3008 (—NH—), 1716, 1681 (—C═O). MS m/z: 357.1 (M$^+$).

EXAMPLE 8

Synthesis of 6-(4-chlorophenyl)-1-(4-methylsulfonyl-phenyl)-1H-pyrimidin-2,4-(1H)-dione

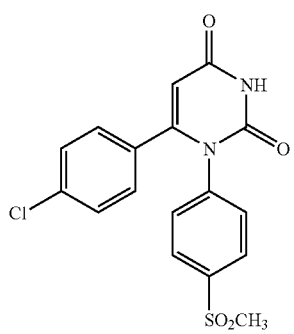

The title compound was prepared from 1-(4-methylsulfanyl-phenyl)-6-(4-chlorophenyl)-1H-pyrimidin-2,4-(1H)-dione (0.5 g, 1.4 mmol) (obtained according to the procedure described in example 3) by following the procedure described in example 6 (0.326 g, 59.3%, mp 294-298° C., purity 97.6% by HPLC). $^1$H-NMR (DMSO-$d_6$): δ 3.20 (s, 3H), 5.76 (s, 1H), 7.24-7.26 (d, 2H), 7.32-7.34 (d, 2H), 7.55-7.57 (d, 2H), 7.82-7.84 (d, 2H), 11.71 (bs, 1H, $D_2O$ exchangeable). IR (KBr) cm$^{-1}$: 3437, 3170, 3049 (—NH—), 1690 (—C═O). MS m/z: 377.1 (M$^+$).

EXAMPLE 9

Synthesis of 4-(2,6-dioxo-3-phenyl-1,2,3,6-tetrahydro-pyrimidin-4-yl)-benzenesulfonamide

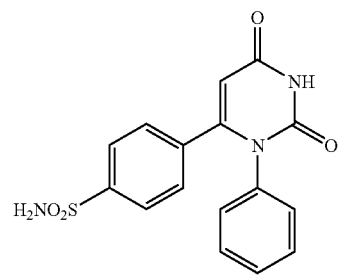

The chlorosulfonic acid (1.18 g, 10 mmol) was added to a solution of 1,6-diphenyluracil (0.2 g, 0.75 mmol) (synthesized according to the procedure given in Harvey I. Skulnick, Heterocycles, 23, (7), pp 1685, 1985) in chloroform (20 ml) and refluxed for 2 hours. The reaction mixture was poured onto ice-water mixture and extracted with ethylacetate. The ethylacetate extract was washed with brine, dried over anhydrous sodium sulphate and concentrated to dryness under reduced pressure. The crude solid thus obtained was taken in tetrahydrofuran (20 ml) and treated with ammonia solution (1 ml) under stirring. The reaction mixture was stirred for 1 hour and concentrated to dryness in vacuum. The product thus obtained was dissolved in ethylacetate, washed with water, brine and dried over anhydrous sodium sulphate. The ethylacetate extract was concentrated to dryness under reduced pressure and purified by column chromatography to yield the title compound (0.1 g, 18.3%). mp: _____.

$^1$H-NMR (DMSO-$d_6$): δ 5.69 (s, 1H), 7.21-7.26 (m, 5H), 7.36-7.46 (m, 4H), 7.65-7.72 (m, 2H), 11.63 (bs, 1H). MS m/z: 344.1 (M$^+$).

Described below are the examples of pharmacological assays used for finding out the efficacy of the compounds of the present invention wherein their protocols and results are provided.

Rat Carrageenan Paw Edema Test

The carrageenan paw edema test was performed as described by Winter et al (Proc.Soc. Exp Biol Me., 111, 544, 1962). Male Wistar rats were selected and the body weight were equivalent within each group. The rats were fasted for eighteen hours with free access to water. The rats were dosed orally with the test compound suspended in vehicle containing 0.5% methylcellulose. The control rats were administered the vehicle alone. After one hour the rats were injected with 0.1 ml of 1% Carrageenan solution in 0.9% saline into the sub plantar surface of the right hind paw. Paw thickness was measured using vernier calipers at 0 time, after 2 and 3 hours. The average of foot swelling in drug treated animals was compared with that of control animals. Anti-inflammatory activity was expressed as the percentage inhibition of edema compared with control group [Arzneim-Forsch/Drug Res 43(I), 1, 44-50,1993; Ottemess and Bliven, Laboratory Models for Testing NSAIDs, In Non-Steroidal Anti-Inflammatory Drugs, (J. Lombardino, ed.1985)]. The data of the selected compounds in this invention are summarized in Table I. In order to evaluate their role on the ulcer formation, the animals were sacrificed by cervical dislocation, the stomach removed and flushed with 1% formalin (10 ml). The stomach was opened along the greater curvature. The haemorrhagic puncta and sulci were identified macroscopically. The presence or absence of stomach lesions was scored. The incidence of ulceration was calculated from the number of rats that showed atleast one gastric ulcer or haemorrhagic erosion.

In vitro Evaluation of Cycloxygenase-2 (COX-2) Inhibition Activity

The compounds of this invention exhibited in vitro inhibition of COX-2. The COX-2 inhibition activity of the compounds illustrated in the examples was determined by the following method.

Human Whole Blood Assay

Human whole blood provides a protein and cell rich milieu appropriate for the study of biochemical efficacy of anti-inflammatory compounds such as selective COX-2 inhibitors. Studies have shown that normal human blood does not contain COX-2 enzyme. This is correlating with the observation that COX-2 inhibitors have no effect on prostaglandin $E_2$ (PGE2) production in normal blood. These inhibitors are active only after incubation of human blood with lipopolysaccharide (LPS), which induces COX-2 production in the blood.

Method

Fresh blood was collected in tubes containing potassium EDTA by vein puncture from male volunteers. The subjects should have no apparent inflammatory conditions and not taken NSAIDs for atleast 7 days prior to blood collection. Blood was treated with aspirin in vitro (10 µg/ml, at time zero) to inactivate COX-1, and then with LPS (10 µg/ml) along with test agents or vehicle. The blood was incubated for 24 h at 37° C., after which the tubes were centrifuged, the plasma was separated and stored at −80° C. (J Pharmacol Exp Ther 271, 1705, 1994; Proc Natl Acad Sci USA 96, 7563, 1999). The plasma was assayed for PGE2 using Cayman ELISA kit as per the procedure outlined by the manufacturer (Cayman Chemicals, Ann Arbor, USA). The plasma was also tested for TNF-α, IL-1β, and IL-6 using appropriate human ELISA kit as per the procedure of manufacturer (Cayman Chemicals, Ann Arbor, USA). Representative results of COX-2 inhibition are shown in Table I.

TABLE I

| Example No. | Conc. (µM) | COX-2 % Inhibition |
| --- | --- | --- |
| 7 | 1 | 40.76 |

Tumor Necrosis Factor Alpha (TNF-α)

This assay determines the effect of test compounds on the production of TNF-α from human monocytes. Compounds were tested for their ability to downregulate the production of TNF-α in activated monocytes. Test compounds were incubated for three, six and twenty four hours with human monocytes. Lipopolysaccharide was used to stimulate the monocytes. The level of TNF-α was quantitated using Enzyme-Linked Immunosorbent assay performed in a 96 well format. Representative results of TNF-α inhibition are shown in Table II.

TABLE II

| Example No. | Conc. (µM) | TNF-α % Inhibition |
| --- | --- | --- |
| 1 | 10 | 48.55 |
| 2 | 10 | 69.31 |
| 6 | 10 | 43.19 |
| 7 | 10 | 57.59 |

Interleukin-6 (IL-6)

This assay determines the effect of test compounds on the production of IL-6 from human monocytes. Compounds are tested for their ability to downregulate the production of IL-6 in activated monocytes. Test compounds were incubated for three, six and twenty four hours with human monocytes. Lipopolysaccharide was used to stimulate the monocytes. The level of Interleukin-6 is quantitated using Enzyme-Linked Immunosorbent assay performed in a 96 well format. Representative results of IL-6 inhibition are shown in Table III.

TABLE III

| Example No. | Conc. (µM) | IL-6 % Inhibition |
| --- | --- | --- |
| 1 | 10 | 80.62 |
| 2 | 10 | 78.56 |
| 6 | 10 | 75.26 |
| 7 | 10 | 81.29 |

Inhibitory Action on Adjuvant Arthritis

Compounds were assayed for their activity on rat adjuvant induced arthritis according to Theisen-Popp et al., (Agents Actions 42, 50-55,1994). Six-seven weeks old, Wistar rats were weighed, marked and assigned to groups [a negative control group in which arthritis was not induced (non-adjuvant control), a vehicle-treated arthritis control group, test substance treated arthritis group]. Adjuvant induced arthritis was induced by an injection of *Mycobacterium butyricum*

(Difco) suspended in liquid paraffin into the sub-plantar region of the right hind paw (J Pharmacol Exp Ther, 284, 714, 1998). Body weight, contra-lateral paw volumes were determined at various days (0, 4, 14, 21) for all the groups. The test compound or vehicle was administered orally beginning post injection of adjuvant and continued for 21 days. On day 21, body weight and paw volume of both right and left hind paw, spleen, and thymus weights were determined. In addition, the radiograph of both hind paws was taken to assess the tibio-tarsal joint integrity. Hind limb below the stifle joint was removed and fixed in 1% formalin saline. At the end of the experiment, plasma samples were analysed for cytokines, interleukins and prostaglandins. The presence or absence of lesions in the stomachs was also observed.

Two-factor ('treatment' and 'time') Analysis of Variance with repeated measures on 'time' were applied to the % changes for body weight and foot volumes. A post hoc Dunnett's test was conducted to compare the effect of treatments to vehicle. A one-way Analysis of Variance was applied to the thymus and spleen weights followed by the Dunnett's test to compare the effect of treatments to vehicle. Dose-response curves for % inhibition in foot volumes on days 4, 14 and 21 were fitted by a 4-parameter logistic function using a nonlinear Least Squares' regression. $ID_{50}$ was defined as the dose corresponding to a 50% reduction from the vehicle and was derived by interpolation from the fitted 4-parameter equation In-vitro Anti-Cancer Activity The compounds of the present invention were also tested for anticancer activity. Each test compound was screened against a battery of 60 human cell lines obtained from eight organs. The cell suspensions were diluted according to the particular cell type and the target cell density (5000-40,000 cells per well based on cell growth characteristics) was added into 96-well micro titer plates. Inoculates were allowed a pre-incubation period of 24 h at 37° C. for stabilization. Dilutions at twice the intended test concentrations were added at time zero in 100 μl aliquots to micro titer plate wells. Usually test compounds were evaluated at five 10-fold dilutions. The highest well concentration used in the test is $10^{-4}$ M. The cells were then incubated in the presence of the test compound for further 48 h in 5% $CO_2$ atmosphere and 100% humidity. After completion of the incubation period the adherent cells were fixed to the plate by means of trichloroacetic acid. After three to five times washing, the cell layer was treated with the protein stain Sulforhodamine B. The optical density, which is proportional to protein mass, was then read by spectrophotometric plate readers at a wavelength of 515 nm.

The invention claimed is:

1. A compound of formula (Ia):

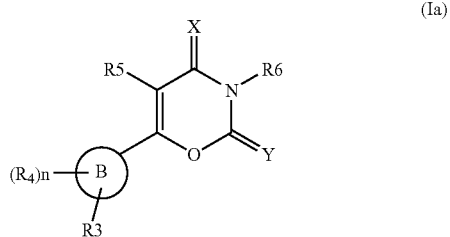

(Ia)

its tautomeric forms, its stereoisomers and their pharmaceutically acceptable salts, wherein X and Y may be same or different and independently represent oxygen, sulfur or NR, wherein R represents hydrogen, hydroxyl, acyl, alkyl, alkoxy, aryl, amino, hydroxylamino, alkylamino, arylamino, acylamino, or alkoxyamino group; the ring represented by B is selected from aryl and heteroaryl; $R^3$ represents $SR^7$, wherein $R^7$ represents alkyl or aryl; $S(O)_pR^8$, wherein $R^8$ represents alkyl, amino or aryl group and p represents an integer of 1 or 2; $R^4$ represents hydrogen, halogen, hydroxyl, nitro, cyano, azido, nitroso, amino, formyl, alkyl, haloalkyl, acyl, alkoxy, monoalkylamino, dialkylamino, acylamino, alkoxycarbonyl, alkylsulfonyl, alkylsulfinyl, alkylthio, sulfamoyl, alkoxyalkyl groups or carboxylic acids or its derivatives; $R^5$ and $R^6$ may be same or different and independently represent hydrogen, halogen, hydroxyl, formyl, cyano, nitroso, nitro, amino, alkyl, acyl, monoalkylamino, dialkylamino, arylamino, acylamino, alkoxyalkyl or $COR^9$, wherein $R^9$ represents hydroxy, amino, halogen, alkoxy, aryloxy, monoalkylamino, dialkylamino, or arylamino groups; n is an integer and represents 0 to 2.

2. A method of reducing inflammation, inhibiting TNF-α, inhibiting 11-6 or inhibiting COX-2 in a mammal comprising administering to the mammal in need thereof an effective amount of pyrimidinedione derivatives of the formula (I)

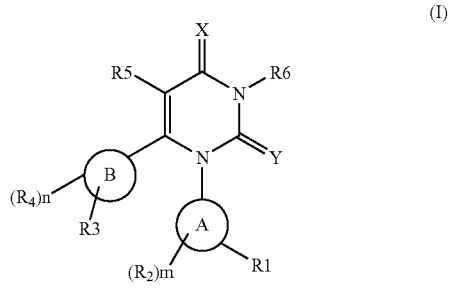

(I)

their their tautomeric forms, their stereoisomers, their solvates, their pharmaceutically acceptable salts and their pharmaceutically acceptable compositions, wherein X and Y may be same or different and independently represent oxygen, sulfur or NR, wherein R represents hydrogen, hydroxyl, acyl, alkyl, alkoxy, aryl, amino, hydroxylamino, alkylamino, arylamino, acylamino, or alkoxyamino group; the rings represented by A and B are selected from aryl and heteroaryl; $R^1$ and $R^3$ are different and represent hydrogen or $SR^7$, wherein $R^7$ represents alkyl or aryl; $S(O)_pR^8$, wherein $R^8$ represents alkyl, amino or aryl group and p represents an integer of 1 or 2; $R^2$ and $R^4$ may be same or different and independently represent hydrogen, halogen, hydroxyl, nitro, cyano, azido, nitroso, amino, formyl, alkyl, haloalkyl, acyl, alkoxy, monoalkylamino, dialkylamino, acylamino, alkoxycarbonyl, alkylsulfonyl, alkylsulfinyl, alkylsulfanyl, sulfamoyl, alkoxyalkyl groups or carboxylic acids or its derivatives; $R^5$ and $R^6$ may be same or different and independently represent hydrogen, halogen, hydroxyl, formyl, cyano, nitro, nitroso, amino, alkyl, acyl, monoalkylamino, dialkylamino, arylamino, acylamino, alkoxyalkyl or $COR^9$, wherein $R^9$ represents hydroxyl, amino, halogen, alkoxy, aryloxy, monoalkylamino, dialkylamino, or arylamino groups; m is an integer and is in the range of 0 to 2; n is an integer in the range of 0 to 2, inclusive.

3. The method as claimed in claim 2, wherein the ring systems represented by A and B are selected from phenyl, naphthyl, pyrrolidinyl, morpholinyl, thiomorpholinyl, piperidinyl, piperazinyl, pyridyl, thienyl, furyl, pyrrolyl, oxazolyl, thiazolyl, imidazolyl, pyrazolyl, oxadiazolyl, thiadiazolyl, tetrazolyl, pyrimidinyl, benzopyranyl, benzofuranyl, benzimidazolyl, benzoxazolyl, benzothiazolyl, benzopyrolyl, benzoxadiazolyl, benzothiadiazolyl, quinolinyl, isoquinolinyl, benzothienyl, benzofuranyl and indolyl.

4. A method of reducing inflammation, inhibiting TNF-α, inhibiting IL-6 or inhibiting COX-2 in a mammal comprising administering to the mammal in need thereof an effective amount of one or more compounds selected from the group consisting of:

1-(4-Methylsulfanyl-phenyl)-6-phenyl-pyrimidin-2,4-(1H)-dione;
6-(4-Methylphenyl)-1-(4-methylsulfanyl-phenyl)-pyrimidin-2,4-(1H)-dione;
6-(4-Ethylphenyl)-1-(4-methylsulfanyl-phenyl)-pyrimidin-2,4-(1H)-dione;
1-(4-Methylphenyl)-6-(4-methylsulfanyl-phenyl)-pyrimidin-2,4-(1H)-dione;
1-(4-Bromophenyl)-6-(4-methylsulfanyl-phenyl)-pyrimidin-2,4-(1H)-dione;
6-(4-Chlorophenyl)-1-(4-methylsulfanyl-phenyl)-pyrimidin-2,4-(1H)-dione;
6-(4-Chloro-3-methylphenyl)-1-(4-methylsulfanyl-phenyl)-pyrimidin-2,4-(1H)-dione;
6-(3-Chloro-4-methylphenyl)-1-(4-methylsulfanyl-phenyl)-pyrimidin-2,4-(1H)-dione;
6-(4-Fluoro-3-methylphenyl)-1-(4-methylsulfanyl-phenyl)-pyrimidin-2,4-(1H)-dione;
6-(4-Fluorophenyl)-1-(4-methylsulfanyl-phenyl)-pyrimidin-2,4-(1H)-dione;
6-(4-Methylsulfanyl-phenyl)-1-phenyl-pyrimidin-2,4-(1H)-dione;
6-(4-Methylphenyl)-1-(3-chloro-4-methylsulfonyl-phenyl)-pyrimidin-2,4-(1H)-dione;
6-(4-Methoxy-3-methylphenyl)-1-(4-methylsulfonyl-phenyl)-pyrimidin-2,4-(1H)-dione;
6-(4-Methylphenyl)-1-(4-methylsulfonyl-phenyl)-pyrimidin-2,4-(1H)-dione;
6-(4-Ethylphenyl)-1-(4-methylsulfonyl-phenyl)-pyrimidin-2,4-(1H)-dione;
6-(4-Chlorophenyl)-1-(4-methylsulfonyl-phenyl)-pyrimidin-2,4-(1H)-dione;
6-(4-Chloro-3-methylphenyl)-1-(4-methylsulfonyl-phenyl)-pyrimidin-2,4-(1H)-dione;
6-(4-Chlorophenyl)-1-(3-methoxy-4-methylsulfonyl-phenyl)-pyrimidin-2,4-(1H)-dione;
6-(3-Chloro-4-methylphenyl)-1-(4-methylsulfonyl-phenyl)-pyrimidin-2,4-(1H)-dione;
6-(4-Fluorophenyl)-1-(4-methylsulfonyl-phenyl)-pyrimidin-2,4-(1H)-dione;
1-(4-Methylsulfonyl-phenyl)-6-phenyl-pyrimidin-2,4-(1H)-dione;
1-(4-Methylsulfanyl-phenyl)-6-(pyridin-2-yl)-pyrimidin-2,4-(1H)-dione;
6-(4-Methylpyridin-2-yl)-1-(4-methylsulfanyl-phenyl)-pyrimidin-2,4-(1H)-dione;
6-(4-Chloropyridin-2-yl)-1-(4-methylsulfanyl-phenyl)-pyrimidin-2,4-(1H)-dione;
6-(4-Methylsulfanyl-phenyl)-1-(pyridin-2-yl)-pyrimidin-2,4-(1H)-dione;
1-(4-Methylsulfonyl-phenyl)-6-(pyridin-2-yl)-pyrimidin-2,4-(1H)-dione;
6-(4-Methylpyridin-2-yl)-1-(4-methylsulfonyl-phenyl)-pyrimidin-2,4-(1H)-dione;
6-(4-Chloropyridin-2-yl)-1-(4-methylsulfonyl-phenyl)-pyrimidin-2,4-(1H)-dione;
4-(2,4-Dioxo-6-(4-methylphenyl)-3,4-dihydro-2H-pyrimidin-1-yl)-benzenesulfonamide;
4-(2,4-Dioxo-6-phenyl-3,4-dihydro-2H-pyrimidin-1-yl)-benzenesulfonamide;
4-[6-(4-Bromo-phenyl)-2,4-dioxo-3,4-dihydro-2H-pyrimidin-1-yl]-benzenesulfonamide;
4-(2,6-Dioxo-3-phenyl-1,2,3,6-tetrahydro-pyrimidin-4-yl)-benzenesulfonamide;
4-(2,6-Dioxo-3-(4-methylsulfanyl-phenyl)-1,2,3,6-tetrahydro-pyrimidin-4-yl)-benzenesulfonamide and
4-[3-(4-Chloro-phenyl)-2,6-dioxo-1,2,3,6-tetrahydro-pyrimidin-4-yl]-benzenesulfonamide.

5. The method of claim 2, wherein the activity of plasma concentration or the production of either or in combination of the following TNF-α, IL-1, IL-6, IL-8 and IL-12 are inhibited.

6. The method of claim 2, wherein prostaglandins production is decreased.

7. The method of claim 2, wherein cyclooxygenase enzyme activity is decreased.

8. The method of claim 4, wherein the activity of plasma concentration or the production of either or in combination of the following TNF-α, IL-1, IL-6, IL-8 and IL-12 are inhibited.

9. The method of claim 4, wherein prostaglandins production is decreased.

10. The method of claim 4, wherein cyclooxygenase enzyme activity is decreased.

* * * * *